(12) United States Patent
Takao et al.

(10) Patent No.: US 6,623,978 B2
(45) Date of Patent: Sep. 23, 2003

(54) OBSERVING TECHNIQUES AND ITS EVALUATION EQUIPMENTS OF RHEOLOGICAL PROPERTIES FOR RESIN POLYMER COMPOSITE FILLED WITH CERAMIC FILLER-POWDER

(75) Inventors: Yasumasa Takao, Aichi (JP); Mutsuo Sando, Aichi (JP); Makio Naito, Aichi (JP)

(73) Assignee: Japan as represented by Secretary of Agency of Industrial Science and Technology, Tokyo (JP)

( * ) Notice: Subject to any disclaimer, the term of this patent is extended or adjusted under 35 U.S.C. 154(b) by 122 days.

(21) Appl. No.: 09/748,003

(22) Filed: Dec. 27, 2000

(65) Prior Publication Data

US 2002/0039794 A1 Apr. 4, 2002

(30) Foreign Application Priority Data

Aug. 16, 2000 (JP) ........................................ 2000-246636

(51) Int. Cl.$^7$ .............................................. G01N 11/00
(52) U.S. Cl. ...................... 436/164; 436/171; 422/68.1; 422/82.05; 422/82.09; 73/866; 73/53.01; 73/54.01
(58) Field of Search .............................. 436/69, 7, 164, 436/171; 73/866, 53.01, 54.01, 54.14; 422/68.1, 73, 82.05, 82.09

(56) References Cited

U.S. PATENT DOCUMENTS 6,199,437 B1 * 3/2001 Kumaraswamy et al. ..... 73/866

FOREIGN PATENT DOCUMENTS

SU     1048372 A  *  10/1983
SU     1173260 A  *  9/1985

OTHER PUBLICATIONS

Yasumasa Takao, et al. "Processing Defects and Their Relevance to Strength in Alumina Ceramics Made By Slip Casting," Journal of the European Ceramic Society, 20, 2000, pp. 389–395.

* cited by examiner

Primary Examiner—Lyle A. Alexander
(74) Attorney, Agent, or Firm—Oblon, Spivak, McClelland, Maier & Neustadt, P.C.

(57) ABSTRACT

This invention relates to a method of measuring a rheological property of a composite filled with particles, and evaluation equipment, in which in situ measurement is performed of the rheological property of a composite filled with particles obtained by mixing a particulate material as raw material with a liquid material, in a condition with the original material structure maintained, without destroying the material by applying external force such as shearing force thereto, comprising a step of measuring the coagulation structure of the particulate material within the composite filled with particles as an anisotropy signal, and a step of employing the amount of this anisotropy as an index of the rheological property value of the composite.

5 Claims, 3 Drawing Sheets

OBSERVING TECHNIQUES AND ITS EVALUATION EQUIPMENTS OF RHEOLOGICAL PROPERTIES FOR RESIN POLYMER COMPOSITE FILLED WITH CERAMIC FILLER-POWDER

BACKGROUND OF THE INVENTION

1. Field of the Invention

The present invention relates to a method of measuring a rheological property of a composite filled with particles obtained by mixing and dispersing a particulate material in a liquid material such as resin and equipment therefor. In more particularly, it relates to a method for measuring a rheological property of a composite filled with particles and evaluation equipment employing, and this method comprises a method wherein a rheological property of a composite filled with particles obtained by mixing a raw-material particulate material with a liquid material is measured in situ in a condition maintaining the original material structure without destroying the material by applying external force such as shearing force thereto, by measuring as an anisotropy signal the coagulation structure of the particulate material within the composite filled with particles, and using the amount of this anisotropy as an index of a rheological property, of the properties of the composite filled with particles.

2. Description of the Related Art

Composite materials filled with particles obtained by mixing and dispersing particulate materials in liquid materials such as resins are employed as insulating materials, electrode/conductive materials, electroviscous fluids, chemical/mechanical grinding slurries, and raw materials for ceramic molding processes such as injection molding and/or cast molding, and also, in recent years, have come to be widely used in sealing materials intended for protecting and insulating semiconductor elements. In particular, with progress in VLSI, in order to achieve increased element fineness, low viscosity/high forming ability of composite materials filled with particles in order to achieve the ability to produce any required shape and/or to enable pouring between minute electrodes is indispensable.

However, scientific study of the field of such composite materials filled with particles is still in its infancy and studies relating to the viscosity and moldability of composite materials filled with particles are based merely on experience. For example, in common methods of evaluation of the rheological properties such as viscosity of a composite filled with particles, this is evaluated indirectly by deduction from primary information such as the particle size distribution of the particulate material constituting the raw material for packing/dispersion. Such methods of evaluation are based on the fact that the viscosity of the particle dispersion material becomes smaller as the particle size of the particulate material that is mixed therein becomes large and the relative surface area becomes small, or that the viscosity becomes lower as the width of the particle size distribution becomes greater. However, in current practically used material systems, products are seldom prepared wherein these factors are individually controlled and owing to the complex mutual interaction of various factors, it is difficult to define conditions such that rheological properties are dominant. It has therefore been pointed out that there are limits to the extent to which it is possible to achieve the accuracy required in an evaluation technique of rheological properties of for example semiconductor sealing materials simply using such conventional discoveries (for example, Shinsuke Hagiwara "The present state of development of semiconductor sealing materials", Plastics, Vol. 49, p. 58, 1998 and Takeshi Kitano "Rheological properties of filler packing polymer melts", Filler, Vol. 3, p. 96, 1998).

As a way of solving this, attempts have been made to construct theoretical hypotheses of the packing structure and dispersion condition of the particulate material in the composite filled with particles, and to correlate these with rheological properties. For example, in the field of wet molding of ceramics there are studies of slurry viscosity hypothesizing the particle structures formed in the molding process (for example, Laid-open Japanese Patent Publication Number 11-304686 (1999) and Ichiro Tsubaki et al. "New method of evaluation of slurries for optimal design of wet molding processes", Journal of the Ceramics Association of Japan (Nippon Seramikusu Gakkai Ronbunshi), Vol. 106, p. 504, 1998). Also, in the field of electroviscous fluids, there are attempts to correlate the relationships between density and current values of mixed particulate materials (for example Laid-open Japanese Patent Publication Number 11-343496 (1999)). Although there are instances where methods such as the above succeed in the case of material systems where the concentration of the particulate material is not particularly large, so that the particle size distribution etc. is simple (if possible monodispersed), they cannot adequately cope with dispersed systems of high particulate material concentration having practically employed particle size distribution and/or surface characteristics (for example, Hiroki Usui "Rheological model for coagulated slurry of monodispersed fine silica particles", Collected Chemical Engineering Papers (Kagaku Kogaku Ronbunshu), Vol, 25, p. 459, 1999)

We have up to the present been unsuccessful in finding any studies in which the secondary structure of particulate materials as described above is actually directly observed in the condition in which the composite filled with particles is employed i.e. in a condition in which the original material structure is maintained. We believe that one reason for this is that no method has been established for observing the internal structure of a dispersion system and correlating this structure with its properties when the liquid material is a dispersion medium. For example, there is the problem that no methodology has been prepared for the application to liquid material systems of methods of measurement using X-ray diffraction equipment, optical microscopes, or scanning electron microscopes (SEM) etc., which are the universal methods in the case of dispersion systems where the dispersion medium of the particulate material is solid (for example ceramic material systems etc.).

Also, in most existing methods of measuring rheological properties, measurement was effected by inserting a stirrer or cantilever of an interatomic force microscope into the composite filled with particles, thereby destroying its structure, and using the shearing force etc. when this was done as an index. Methods existed in which structural analysis was conducted in a non-contacting condition with the composite filled with particles still in the condition in which it is actually used, by employing an electron beam or X-ray diffraction, in the case of the particulate material on its own, or by employing polarization or interference of light waves, in the case of the liquid material on its own. However, no method employing these has been found in the case of a composite filled with particles, which is a material in which these are mixed together. The case when the liquid material is a resin-based material can be regarded as one type of polymer material. In polymeric material systems, typically use is made of polarized light observation for evaluation of the photoelasticity characteristic with applied stress, measurement of the birefringence of a plastic lens, or evaluation of molecular alignment characteristics in liquid crystal materials. However, no attempts have been made to employ this for evaluation of the characteristics of particles, rather than resin, in resin composite materials filled with particles·dispersion materials. The reason for this is believed to be that the particulate materials that are generally employed in this material field are amorphous $SiO_2$ particles and it was not intuitively anticipated that these methods of observation could be applied to materials having an isotropic crystalline structure (or not having a crystalline structure).

In order to overcome the defects possessed by such conventional measurement techniques for composite materials filled with particles, the present invention was developed taking as technical problem the provision of a method of measurement of rheological properties of composite materials filled with particles and evaluation equipment employing this principle of measurement under the following necessary conditions: in situ measurement of the rheological property of the composite filled with particles in a condition in which the original material structure is maintained without destroying the material by applying external force such as shearing force; measurement of non-uniform structure i.e. coagulation structure of the particulate material within the composite filled with particles as an anisotropy signal; and employment of the amount of this anisotropy as an index of the rheological property value of the composite filled with particles properties.

The present inventors noted that when a composite filled with particles was prepared the packing structure of the particulate material became non-uniform or, when secondary coagulation was created, the alignment of the polymers was increased by application of stress to the surrounding liquid material compared with regions where such stress was not applied. Also, it was thought that bubbles might be produced in the region of the interface between the particulate material and the liquid material, or the interface itself (connection surface of different refractive indices) constituted by the materials of different types might constitute an optically anisotropic body. It was conceived that it should be possible to measure rheological properties of composite materials filled with particles, as these would provide structures capable of being detected by crystallographic measurement methods or optical distortion, offering the possibility of performing evaluation by observation at diagonally opposite positions, and as it was thought that the (apparent) density of the particulate material would be raised by inclusion of liquid material in the packing/dispersion structure of the particulate material or that constituents of the dispersion medium not contributing to shearing would be increased on the manifestation of viscosity.

As a result of various studies aimed at implementing the above concept concerning the effect of primary characteristics of the particles such as the particle size distribution of the particulate material used as filler, the method of preparation and the evaluation test conditions etc., the present inventors discovered that non-uniform structure of a composite filled with particles could be measured by utilizing the optical anisotropy or crystallographic anisotropy possessed by the liquid material or the particle/liquid interface and that the packing structure or condition of dispersion of the particulate material could be identified using the results of such measurement as an index i.e. that there was a unique correlation of the condition of dispersion of the fine particles measured in terms of the aforesaid anisotropy with the rheological properties of the composite filled with particles, and perfected the present invention based on this discovery.

SUMMARY OF THE INVENTION

There is provided a measurement technique for rheological properties of a composite filled with particles and evaluation equipment using this.

This invention relates to a method of measuring a rheological property of a composite filled with particles, and evaluation equipment, in which in situ measurement is performed of the rheological property of a composite filled with particles obtained by mixing a particulate material as raw material with a liquid material, in a condition with the original material structure maintained, without destroying the material by applying external force such as shearing force thereto, comprising a step of measuring the coagulation structure of the particulate material within the composite filled with particles as an anisotropy signal, and a step of employing the amount of this anisotropy as an index of the rheological property value of the composite. This is beneficial in particular as a method of evaluation of semiconductor sealing material/manufacturing process control technique in that it makes it possible to provide a method of in situ measurement and evaluation equipment therefor in a condition in which the original material structure is maintained without destroying the material by applying external force such as shearing force to the composite filled with particles or without performing special processing.

DETAILED DESCRIPTION OF THE INVENTION

An object of the present invention is to provide a method and evaluation equipment using the method for measuring a rheological property of a composite filled with particles in a non-contacting condition with the measurement means with the composite filled with particles still in the condition in which it is actually used by identifying the dispersion condition of the particulate material and liquid material using as an index the result of measurement achieved by actual measurement and detection of the packing structure and/or dispersion condition of the particulate material in the composite filled with particles by utilizing optical anisotropy or crystallographic anisotropy possessed by the liquid material and/or particle/liquid interface, which was hitherto only capable of being theoretically hypothesized.

In order to realize the above object, according to the present invention, the following constitution is adopted:

(1) A method of measuring a rheological property of a composite filled with particles in which in situ measurement is performed of the rheological property of a composite filled with particles obtained by mixing a particulate material as raw material with a liquid material, in a condition with the original material structure maintained, without destroying the material by applying external force such as shearing force thereto, which comprises a step of measuring the coagulation structure of the particulate material within the composite filled with particles as an anisotropy signal, and a step of employing the amount of this anisotropy as an index of the rheological property value of the composite material.

(2) The method of measuring a rheological property of a composite filled with particles according to (1) above, wherein the coagulation structure of the particulate material is measured by utilizing crystallographic or optical anisotropy obtained using diffraction of electron beam or X-ray, or polarization/interference of light waves.

(3) The method of measuring a rheological property of a composite filled with particles according to (1) above, wherein the coagulation structure of the particulate material is measured by utilizing photoelasticity based on local rearrangement of liquid material molecules, or the difference of refractive indices of the particulate material and the liquid material.

(4) The method of measuring a rheological property of a composite filled with particles according to (1), (2) or (3) above, wherein the particulate material is an $SiO_2$-based material or AlN-based material.

(5) The method of measuring a rheological property of a composite filled with particles according to (1), (2) or (3) above, wherein the liquid material is a resin-based material.

(6) Equipment for measuring and evaluating a rheological property of a composite filled with particles, which is used in the method of measurement claimed in any of (1) to (5) above, which comprises as structural elements two polarizing elements, a light source or electron beam source, means for observing a transmitted image, and means for arranging a sample, wherein a thin strip sample for transmission observation is arranged between the two polarizing elements, monochromatic light polarized by the first polarizing element is directed onto the sample, and subjected to double refraction at optically anisotropic regions such as coagulations in the sample, then re-polarized by the second polarizing element, and observed by the transmitted image observation means to measure and evaluateoptical behavior thereof such as diagonally opposite positions or interference.

(7) The equipment for evaluation according to (6) above, wherein the sample is a composite filled with particles produced in thin strip form of a thickness allowing monochromatic light from a light source or electron beam source to be transmitted through the composite.

(8) The equipment for evaluation according to (6) above, wherein halogen light is directed on the sample.

DESCRIPTION OF THE PREFERRED EMBODIMENTS

Figure 1:
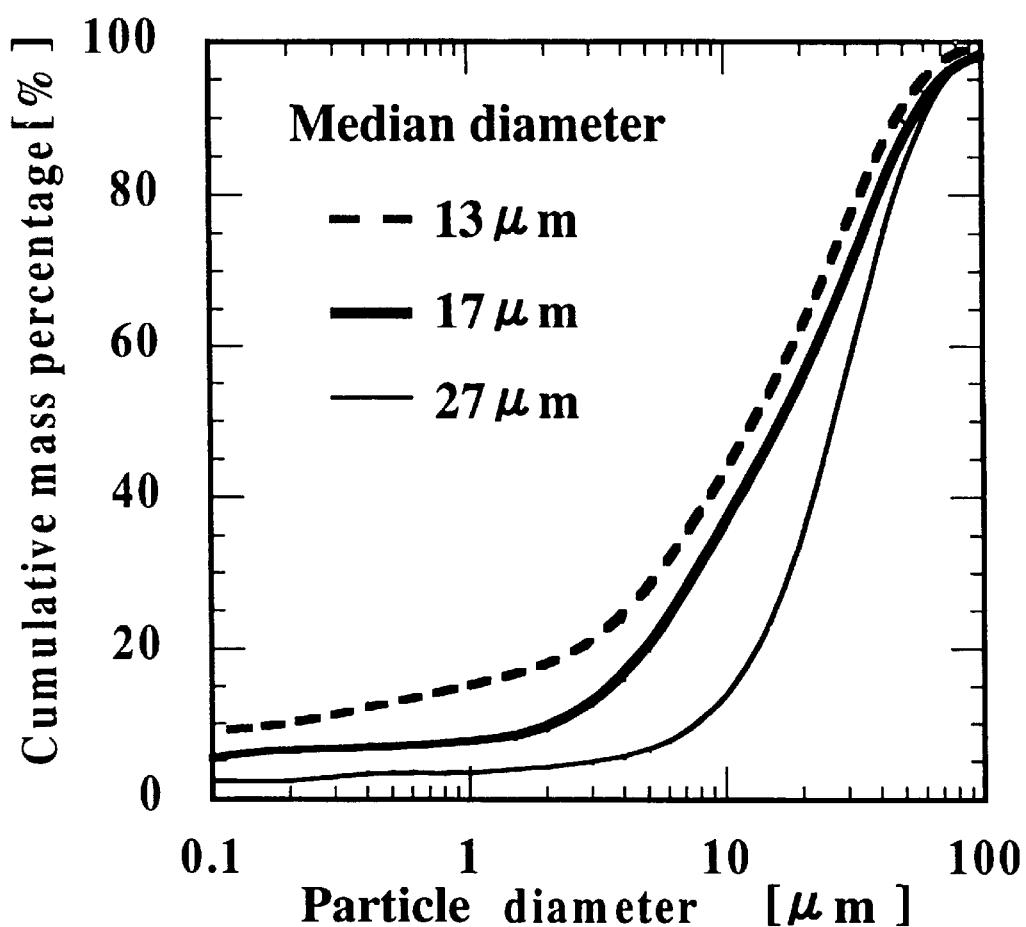
FIG. 1 illustrates the particle size distribution of three types of amorphous/spherical $SiO_2$ particles used in the examples.

The invention is described in further detail below.

The chief features of the present invention consist in the measurement of non-uniform structures of a composite filled with particles in the form of an anisotropy signal, and for this purpose, measurement of coagulation structures of the particulate material by utilizing crystallographic or optical anisotropy, the employment of this anisotropy amount as an index of a rheological property value of the composite filled with particles, and identification and evaluation thereby of the internal structure of the composite filled with particles; specifically, the packing structure and/or dispersion condition of the particulate material in the composite filled with particles is actually measured by utilizing the optical anisotropy or crystallographic anisotropy possessed by the liquid material and/or particle/liquid interface, and a rheological property such as viscosity of the composite filled with particles is identified and evaluated by using the results of this measurement as an index of the rheological property value.

For example $SiO_2$ or AlN, which are commonly used in sealing materials for semiconductor elements, may suitably be employed as the particulate material according to the present invention; apart from these, for example $Al_2O_3$, SiC, $Si_3N_4$ or other oxides, or metals such as Au, Ag, Pd, Pt, Cu, Al, or Au—Pd may of course be employed without any particular restriction as to the type of these. Also, there is no restriction concerning crystallinity; evaluation can be performed easily for crystalline particles or as described above even for amorphous systems.

As the liquid material constituting the medium, suitable examples that may be given include water such as ionized water or distilled water, organic non-aqueous materials such as ethanol and, in addition, resins such as for example resol-type or novolak-type phenolic resins, bisphenolic cresol-novolak multi-functional type epoxy resins, halogenated resins etc., resin materials that are solid at ordinary temperature, and resin materials of liquid type at ordinary temperature that are commonly used as sealing materials for second generation semiconductor elements may suitably be employed; however, other liquid materials may also be employed: there is no particular restriction regarding type.

As the method of preparing the composite filled with particles, various types of compounding techniques etc. such as for example methods of mixing using a kneader, biaxial mill, 3-roll mill, Henschel mixer or planetary motion, mechanical compounding methods using pulverization and/or shearing stress (solid phase methods), liquid phase methods using uniform dispersion of a plurality of constituents in a liquid, or gaseous phase methods using inertial force etc. in a gas maybe employed without any particular restriction: the present invention may be applied to composite filled with particles prepared by any of these methods.

As a specific example of a composite filled with particles to which the present invention may be applied, there may be mentioned semiconductor sealing material tablets formed by premixing of $SiO_2$ particles of polymerization ratio 70 to 90% (with respect to the liquid material) and novolak-based phenolic resin with plasticiser, followed by kneading in a kneader heated to 150 to 180° C. to produce a plate-shaped composite molding, which is then pulverized to obtain a granular powdered raw material which is molded into pellets.

As the method and equipment for observing the internal structure of the composite filled with particles, any suitable method and equipment can be employed based on a measurement principle and detection source having wave motion properties whereby non-contacting measurements of the composite filled with particles can be performed. For example, utilization of an electron microscope and/or X-ray/electron beam diffraction, which are frequently employed with particulate materials, or utilization of an optical system, which is frequently employed with liquid materials, may be mentioned. A convenient method and equipment that do not require adjustment of atmosphere etc. which may be mentioned are for example a method and equipment using two polarizing elements and polarizing monochromatic light by the first polarizing element and directing it onto the composite filled with particles, where it is subjected to double refraction at optically anisotropic regions such as coagulations in the dispersion system, before being re-polarized by the second polarizing element, wherein optical behavior such as the diagonally opposite positions or interference is measured and evaluated; however, there is no restriction thereto.

As a specific example of a construction of the equipment employed in the measurement method of the present invention, there may be mentioned an example construction comprising a device for measuring and evaluating optical behavior such as diagonally opposite positions and/or interference including as structural elements two polarizing elements, a light source or electron beam source, means for observing a transmitted image, and means for arranging a sample, in which a thin strip sample for transmission observation is arranged between the two polarizing elements, monochromatic light polarized by the first polarizing element is directed onto the sample, and subjected to double refraction at optically anisotropic regions such as coagulations in the sample, then re-polarized by the second polarizing element and observed by the transmitted image observation means; a device for observing the composite filled with particles which has been processed into the form of a sheet by fine adjustment of the amount of polarization by a polarizing microscope; and means whereby, after kneading in a kneader in the aforesaid semiconductor sealing material tablets manufacturing process, or in a production line after molding to pellet form, this is subjected to in situ measurement by arranging a polarizing element as a measurement device, and is evaluated without destroying the tablet, and only defective products are removed.

There is no particular restriction regarding the rheological property that is to be the subject of the evaluation, so long as it can be ascertained from the dispersion condition/structure of the particulate material and liquid material. Typical examples that may be mentioned include non-Newtonian viscosity such as the coefficient of viscosity by the biaxial cylinder test method (dynamic coefficient of viscosity, or static coefficient of viscosity if the shearing speed is 0), creep characteristic, thixotropy, rheoplexy, and dilatancy, or interface properties of the particulate material and liquid material.

EXAMPLES

Next, a specific description of the present invention is given with reference to examples thereof; however, the present invention is not restricted in any way by the following examples.

Examples (1) Method

As a particulate material, there were employed amorphous/spherical $SiO_2$ particles having three types of mean particle size (13 $\mu$m, 17 $\mu$m and 27$\mu$m) and particle size distribution, of mean particle size between 10 or more and several tens of $\mu$m and manufactured in a process of melting commonly-used silicon oxide raw material. The mean particle size and particle size distribution of these particles is shown in Table 1 and FIG. 1. Next, as liquid material, bisphenol A type liquid epoxy resin was employed; the respective $SiO_2$ particles and the bisphenol A type liquid epoxy resin were mixed in a weight ratio of 70% of the particles with respect to the resin, kneaded for 5 minutes with a rate of revolution of 1800 rpm and rate of rotation of 600 rpm to produce a resin composite filled with particles.

Next, in order to measure the packing structure and dispersion condition of the particulate material in a resin composite filled with particles by utilizing optical anisotropy of the composite filled with particles, observation was conducted by arranging the composite filled with particles between two polymer polarization plates and passing halogen light therethrough.

|  | Coefficient of viscosity (shearing rate 20 s$^{-1}$) | Coefficient of viscosity (shearing rate 300 s$^{-1}$) | Coefficient of viscosity (shearing rate 600 s$^{-1}$) |
| --- | --- | --- | --- |
| Mean particle size 13 $\mu$m $SiO_2$ particles | 1.3 Pa · s | 1.2 Pa · s | 1.1 Pa · s |
| Mean particle size 17 $\mu$m $SiO_2$ particles | 1.0 Pa · s | 0.9 Pa · s | 0.8 Pa · s |
| Mean particle size 27 $\mu$m $SiO_2$ particles | 2.1 Pa · s | 1.8 Pa · s | 1.4 Pa · s |

(2) Measurement of Coefficient of Viscosity

In order to obtain actually measured values, the coefficient of viscosity of the composite filled with particles was measured with shearing rates of 0 to 600 s$^{-1}$ at 80° C. As typical examples, the viscosity coefficients at shearing rates of 20 s$^{-1}$, 300 s$^{-1}$ and 600 s$^{-1}$ are shown in Table 1. Based on previous information, it would be expected that the viscosity of the composite filled with particles should be lower for increased particle size of the admixed particulate material and smaller relative surface area thereof, or for greater width of the particle size distribution. However, the resin composite filled with particles employing particles of mean particle size 27 $\mu$m had the highest coefficient of viscosity even though it had the largest particle size of the three. Also, the resin composite filled with particles using particles of mean particle size 13 $\mu$m had a higher coefficient of viscosity than that of the resin composite filled with particles using particles of mean particle size 17 $\mu$m even though it had the widest particle size distribution of the three (Table 1 and FIG. 1).

The rheological properties of the above resin composite materials filled with particles are difficult to evaluate and understand by the conventional methods.

(3) Results

Figure 2A:
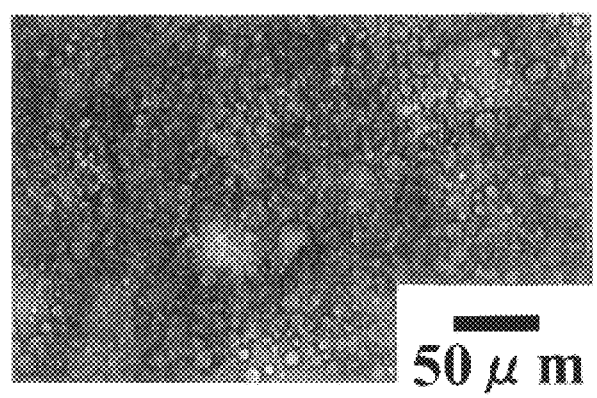
FIGS. 2(A–C) shows a photograph of a transmission observation image of a resin composite filled with particles·dispersion material (a): using particles of mean particle size 13 μm, b): using particles of mean particle size 17 μm, c): using particles of mean particle size 27 μm) obtained using ordinary light.
Figure 2B:
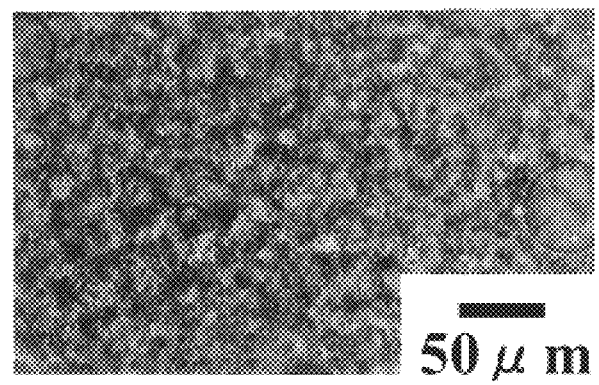
Figure 2C:
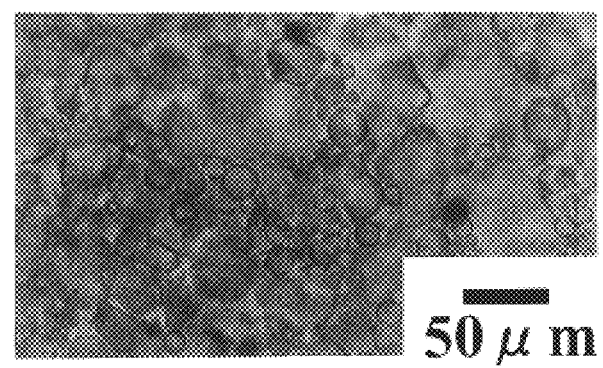

FIG. 2 shows examples of particle/resin dispersion system transmission images representing measurement results obtained using ordinary light. In these, the spherical gray-colored portions indicate the $SiO_2$ particles, while the dark gray-colored portions around these are believed to represent the resin. Of these three types, in the case of the resin composite filled with particles using particles of mean particle size 17 $\mu$m that showed the lowest viscosity, when the same volume was observed, comparatively more resin portion was observed than in the case of the resin composite filled with particles using the other types of particles i.e. it was confirmed that this appears to be uniformly distributed in the entire dispersion system.

Figure 3A:
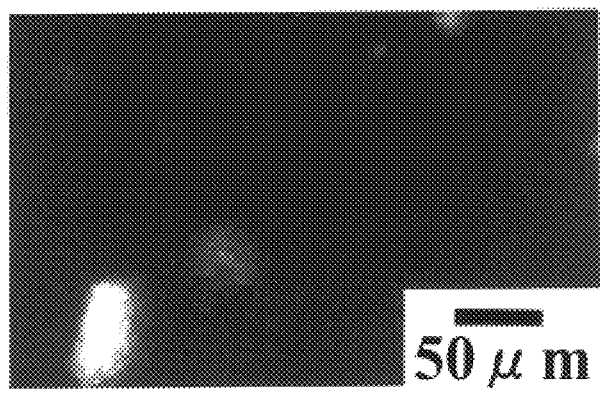
FIGS. 3(A–C) shows a photograph of a transmission·polarization image of a resin composite filled with particles·dispersion material (a): using particles of mean particle size 13 μm, b): using particles of mean particle size 17 μm, c): using particles of mean particle size 27 μm).
Figure 3B:
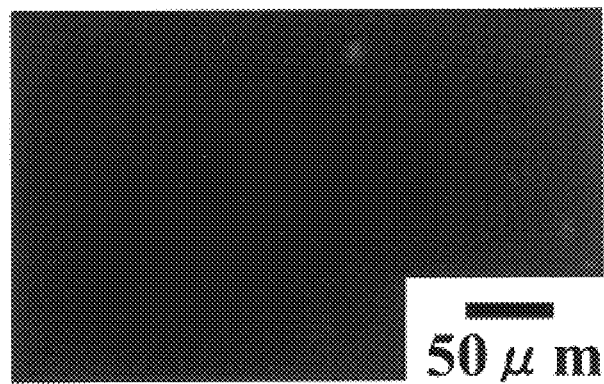

FIG. 3 shows the results of measurement using the method of the present invention. Example photographs of transmission-polarization images of resin composite filled with particles-dispersion systems are shown. Of these three types, it was found that the optical anisotropy detected as bright white portions was comparatively less in the case of the resin composite filled with particles using particles of mean particle size 17 µm that showed the lowest viscosity (FIG. 3b)).

Figure 3C:
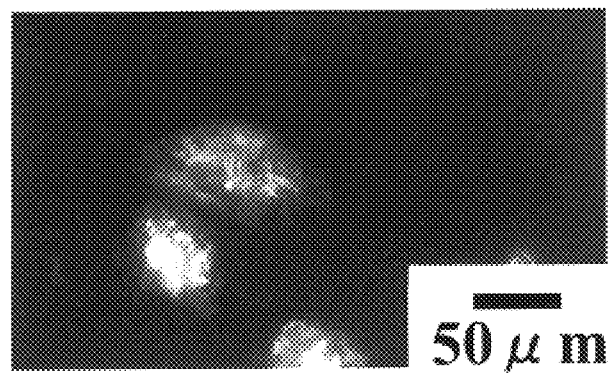

However, in the case of the other types of particles, greater brightness was detected in the cases where the coefficient of viscosity was larger (FIGS. 3a, 3c). In respect of these, the rheological properties of the composite materials filled with particles can be understood if the explanation is adopted that the liquid material is enveloped in the packing/dispersion structure of the particulate material that is detected, resulting in a higher (apparent) concentration of the particulate material, or increasing the amount of dispersion medium constituent that does not contribute to shearing when viscosity appears. As a result of identifying the packing structure and/or dispersion condition of the particulate material using this transmission observation image as an index, it was concluded that aunique correlation could be obtained between this and the rheological properties of the composite filled with particle and that the rheological properties of the composite filled with particles could be determined by identifying the packing structure and dispersion condition of the particulate material using this transmission observation image as an index.

According to the present invention, the noteworthy benefits are presented that 1) rheological properties such as viscosity of a composite filled with particles can be measured by utilizing the fine particle dispersion condition measured in terms of optical anisotropy (light points in polarized light observation), 2) it is possible to measure the rheological properties by ascertaining the internal structure of the particulate material (packing structure or dispersion condition of the particulate material) without either destroying this structure by applying external force by stirring the particle dispersion material using for example a stirrer or performing special processing thereon, in the natural condition of the dispersion system i.e. in situ or in a non-contacting condition, by measurement based on its optical anisotropy, 3) a method can be provided in which the amount of anisotropy is utilized as a rheological index by measuring the non-uniform structure of the dispersion material as an anisotropy signal, 4) a method and evaluation equipment therefor can be provided whereby a rheological property of a composite filled with particles is measured using the aforementioned measurement principle and 5) the aforementioned method is well suited in particular as a method of evaluating semiconductor sealing materials.

What is claimed is:

1. A method of measuring a rheological property of a composite filled with particles in which in situ measurement is performed of the rheological property of a composite filled with particles obtained by mixing a particulate material as raw material with a liquid material, in a condition with the original material structure maintained, which comprises a step of:

mixing a particulate material with a resin material to produce a resin composite filled with particles, transmitting a light from a light source through said composite, observing transmission polarization images of the resin composite filled with particles, and identifying the packing structure and dispersion condition of the particulate material using the transmission polarization images as an index to determine the rheological properties of the composite filled with particles.

2. The method of measuring a rheological property of a composite filled with particles according to claim 1, wherein the particulate material is an $SiO_2$-based material or AlN (Aluminum nitride)-based material.

3. Equipment for measuring and evaluating a rheological property of a composite filled with particles, which is used in the method of measurement of a rheological property of a composite filled with particles in which a particulate material is mixed with a resin material to produce a resin composite filled with particles, a light from light source is transmitted through the said composite, transmission polarization images of the resin composite filled with particles are observed, and the packing structure and dispersion condition of the particulate material are identified using the transmission polarization images as index to determined the rheological properties of the composite filled with particles, which comprises as structural elements two polarizing elements, a light source or electron beam source, means for observing a transmitted image, and means for arranging a sample, wherein a sample for transmission observation is arranged between the two polarizing elements, monochromatic light polarized by the first polarizing element is directed onto the sample, and subjected to double refraction at optically anisotropic regions such as coagulations in the sample, then re-polarized by the second polarizing element, and observed by the transmitted image observation means to measure and evaluateoptical behavior thereof such as diagonally opposite positions or interference.

4. The equipment for evaluation according to claim 3, wherein the sample is a composite filled with particles produced in thin strip form of a thickness allowing monochromatic light from a light source or electron beam source to be transmitted through the composite.

5. The equipment for evaluation according to claim 3, wherein halogen light is directed on the sample.

* * * * *